(12) United States Patent
Luo et al.

(10) Patent No.: US 12,247,009 B2
(45) Date of Patent: Mar. 11, 2025

(54) CROSSLINKERS FOR MASS SPECTROMETRIC IDENTIFICATION AND QUANTITATION OF INTERACTING PEPTIDES

(71) Applicant: Institute for Systems Biology, Seattle, WA (US)

(72) Inventors: Jie Luo, Seattle, WA (US); Jeff Ranish, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 1638 days.

(21) Appl. No.: 16/083,397

(22) PCT Filed: Mar. 10, 2017

(86) PCT No.: PCT/US2017/021946
§ 371 (c)(1),
(2) Date: Sep. 7, 2018

(87) PCT Pub. No.: WO2017/156480
PCT Pub. Date: Sep. 14, 2017

(65) Prior Publication Data
US 2019/0084929 A1 Mar. 21, 2019

Related U.S. Application Data

(60) Provisional application No. 62/306,555, filed on Mar. 10, 2016.

(51) Int. Cl.
| | |
|---|---|
| *C07D 207/416* | (2006.01) |
| *C07D 207/46* | (2006.01) |
| *C07D 513/04* | (2006.01) |
| *G01N 33/60* | (2006.01) |
| *G01N 33/68* | (2006.01) |

(52) U.S. Cl.
CPC ....... *C07D 207/416* (2013.01); *C07D 207/46* (2013.01); *C07D 513/04* (2013.01);
(Continued)

(58) Field of Classification Search
CPC .............. C07D 207/416; C07D 207/46; C07D 513/04; G01N 33/60; G01N 33/6845;
(Continued)

(56) References Cited

U.S. PATENT DOCUMENTS

| | | |
|---|---|---|
| 8,535,948 B2 | 9/2013 | Ranish et al. |
| 2010/0248261 A1 | 9/2010 | Ranish et al. |

(Continued)

OTHER PUBLICATIONS

Petrotchenko et al. (Molecular & Cellular Proteomics, 2011, 10: 10.1074/mcp.M110.001420, pp. 1-8) (Year: 2011).*

(Continued)

*Primary Examiner* — Jeremy C Flinders
(74) *Attorney, Agent, or Firm* — Morrison & Foerster LLP

(57) ABSTRACT

Crosslinking molecules that permit efficient identification of specifically associated proteins and the sites of crosslinking in biological or other samples include two cleavable bonds that are cleavable under the same conditions as peptide bonds in mass spectrometric determinations. Sets of the invention crosslinkers may be provided with isobaric labels containing reporter ions of differing molecular weights to permit relative quantitation of crosslinked protein pairs.

18 Claims, 6 Drawing Sheets

Specification includes a Sequence Listing.

(52) U.S. Cl.
CPC ......... *G01N 33/60* (2013.01); *G01N 33/6845* (2013.01); *G01N 33/6848* (2013.01); *G01N 33/6851* (2013.01); G01N 2458/15 (2013.01); G01N 2560/00 (2013.01)

(58) Field of Classification Search
CPC ........... G01N 33/6848; G01N 33/6851; G01N 2458/15; G01N 2560/00
See application file for complete search history.

(56) References Cited

U.S. PATENT DOCUMENTS

| | | |
|---|---|---|
| 2010/0261279 A1 | 10/2010 | Ranish et al. |
| 2012/0322978 A1 | 12/2012 | Huang |
| 2014/0206091 A1 | 7/2014 | Gunawardena et al. |

OTHER PUBLICATIONS

Chavez et al., "Protein interactions, post-translational modifications and topologies in human cells," Mol Cell Proteomics (2013) 12(5):1451-1467.

Chowdhury et al., "Collisionally Activated Dissociation and Electron Capture Dissociation of Several Mass Spectrometry-Identifiable Chemical Cross-Linkers," Anal Chem (2006) 78(24):8183-8193.

Luo et al., "An integrated chemical cross-linking and mass spectrometry approach to study protein complex architecture and function," Mol Cell Proteomics (2012) 11(20:M111.008318.

Petrotchenko et al., "Isotopically Coded Cleavable Cross-linker for Studying Protein-Protein Interaction and Protein Complexes," Mol Cell Proteomics (2005) 4(8):1167-1179.

Rinner et al., "Identification of cross-linked peptides from large sequence databases," Nat Methods (2008) 5(4):315-318.

Ross et al., "Multiplexed protein quantitation in *Saccharomyces cerevisiae* using amine-reactive isobaric tagging reagents," Mol Cell Proteomics (2004) 3(12):1154-1169.

Sinz et al., "Mapping protein interfaces by a trifunctional cross-linker combined with MALDI-TOF and ESI-FTICR mass spectrometry," J Am Soc Mass Spectrom (2005) 16:1921-1931.

Walzthoeni et al., "False discovery rate estimation for cross-linked peptides identified by mass spectrometry," Nat Methods (2012) 9(9):901-903.

Zhang et al., "Identification of protein-protein interactions and topologies in living cells with chemical cross-linking and mass spectrometry," Mol Cell Proteomics (2009) 8(3):409-420.

* cited by examiner

CROSSLINKERS FOR MASS SPECTROMETRIC IDENTIFICATION AND QUANTITATION OF INTERACTING PEPTIDES

REFERENCE TO RELATED APPLICATIONS

This application is the national phase of PCT application PCT/US2017/021946 having an international filing date of 10 Mar. 2017, which claims priority from provisional application U.S. Ser. No. 62/306,555 filed Mar. 10, 2016. The contents of these applications are incorporated herein by reference.

STATEMENT OF RIGHTS TO INVENTIONS MADE UNDER FEDERALLY SPONSORED RESEARCH

This work was supported in part by National Institutes of Health (NIH) Grant Nos. P50GM076547 and R21CA175849. The U.S. government has certain rights in this invention.

INCORPORATION BY REFERENCE OF SEQUENCE LISTING

The present application is being filed along with a Sequence Listing in electronic format. The Sequence Listing is provided as a file entitled 655652005500SeqList.TXT, created Jul. 29, 2020 which is 8,177 bytes in size. The information in the electronic format of the Sequence Listing is incorporated by reference in its entirety.

TECHNICAL FIELD

The invention is in the field of protein analysis. More specifically, it concerns crosslinkers that can be employed to identify protein-protein interactions in biological samples. By suitable labeling, the interacting proteins can also be quantitated and the quantitation can be multiplexed.

BACKGROUND ART

Most proteins function through specific and regulated interactions with one another. Knowledge of the proteins that participate in protein-protein interactions, and the sites of the interactions is thus essential for understanding biological processes and disease mechanisms. For example, a disease state such as cancer can result from the inappropriate interaction of two or more proteins. Accordingly, knowledge of key protein-protein interaction interfaces is of high interest because this information can be used to guide the design of drugs that target these interfaces for therapeutic benefit.

Many methods have been developed to study protein-protein interactions and corresponding protein structures, such as X-ray crystallography, nuclear magnetic resonance (NMR), surface plasma resonance (SPR), and the yeast two-hybrid system (Y2H); Co-immunoprecipitation and mass spectrometry (Co-IP MS) has also been used.

Of importance to the present invention is chemical cross-linking/Mass Spectrometry (CXMS).

In CXMS, a crosslinking molecule is used to tie together proteins that are sufficiently proximal to interact and thus preserve the interaction for determination of the sequences of the interacting proteins and the sites of crosslinking using mass spectrometry. Clearly, however, this method is complicated by the complex nature of biological samples. One approach to simplifying this technique is to enrich the sample in only crosslinked proteins/peptides by employing affinity ligands into the crosslinkers thus enabling retrieval only of crosslinked peptides. This is described, for example, in Luo, et al., *Mol. Cell. Proteomics* (2012) 11:M111.008318.; Sinz, et al., *J. Am. Soc Mass Spectrom.* (2005) 16:1921-1931; and Chowdhury, et al., *Anal. Chem.* (2006) 78:8183-8193. An earlier patent of the inventors herein, U.S. Pat. No. 8,535,948, describes crosslinkers where the linking groups themselves provide affinity ligands that permit this enrichment.

Isotope coded crosslinkers or peptides have been used to generate lists for targeting MS analysis of the crosslinked peptides or to facilitate the identification of crosslinked peptides by comparing the light and heavy fragment spectra (Petrochenko, E. V., et al., *Mol Cell Proteomics* 4 (2005) 4:1167-1179; Rinner, et al., *Nat. Methods* (2008) 5:315-318; Chavez, et al., *Mol. Cell Proteomics* (2013) 12:1451-1467; Zhang, et al., *Mol. Cell Proteomics*. (2009) 8:409-420; Walzthoeni, et al., *Nat. Methods* (2012) 9:901-903.

Even with these improvements, however, confident identification of crosslinked peptides is challenging due to the exponential increase in database search space that occurs when considering all possible pairs of candidate peptides that can add up to the measured mass of the crosslinked peptide. That is, using most current techniques, the database search space cannot be limited by the masses of the individual peptides that comprise the crosslinked pair because most of the techniques so far employed have not made this information available. Only a few strategies have been developed to facilitate the detection and/or identification of each individual peptide in the crosslinked peptide pair.

U.S. patent application 2014/0206091, for example, to Gunawardena, et al., discloses crosslinking molecules that can bind proteins or peptides where the crosslinker contains a dithiol linkage separating a deuterated and non-deuterated form of the same linking molecule. The disulfide bond is preferentially cleaved in the method described in this application thus yielding doublets that permit the molecular weight of each of the crosslinked peptides to be determined in the MS2 spectrum. In this method, the sample is crosslinked and treated with proteases as is typical in mass spectral techniques so that the first spectrum determined, MS1, provides the molecular weight of the two peptides attached to the crosslinker. We note however that typically protein samples are treated with reducing agents prior to MS analysis to reduce disulfide bonds which are subsequently covalently modified with an alkylating agent. This is not possible when using the crosslinker described by Gunawardena because the reducing agent would break the disulfide bond in the crosslinker. Following cleavage of the disulfide bond during MS analysis, the MS2 spectrum permits determination of the molecular weight of each "half" of the cleaved crosslinker bound to peptide. Because the peptide bonds themselves are not cleaved in the step between MS1 and MS2, a different dissociating technique is used to obtain the fragmentation pattern for the individual peptides which thus requires a subsequent MS3 spectrum.

As will be seen below, the present invention crosslinkers eliminate the necessity for obtaining an MS3 spectrum and, further, offer the possibility of the added advantage of enriching the sample in crosslinked peptides, as well as being compatible with typical workflows for analysis of protein samples by mass spectrometry.

In addition, a set of at least two of the crosslinkers of the invention may be provided with suitable isobaric labels containing reporter ions which permits relative quantitation based on the mass spectrum and thus provides a measure of the relative levels of the crosslinked proteins in multiple samples. These labels are isobaric but have reporter ions of different molecular weight in a set of crosslinkers as described in Ross, P L, et al. *Mol. Cell. Proteomics* (2004) 3:1154-1169.

DISCLOSURE OF THE INVENTION

The crosslinkers of the invention are characterized by having two cleavable bonds that are broken under the same conditions of dissociation as the peptide bonds in the coupled peptides, and wherein the portion of the crosslinker between said two bonds provides for attachment of an optional moiety used for enrichment of the crosslinker-modified peptides or for attachment of a reporter ion which may be included in an isobaric label, thus located so as not to destroy the formation of doublets generated by employing symmetric structurally identical linkers that differ only in mass.

Thus, the invention is directed to crosslinkers for identifying specifically interacting proteins by mass spectrometry (MS) which crosslinker has the formula (1):

wherein each protein binding group (PBG) reacts with an amino, sulfhydryl, hydroxyl or carboxyl group; $X^1$ and $X^2$ are structurally identical linkers containing 3-15 linking member atoms selected from C, N, O and S, and wherein $X^1$ and $X^2$ contain different isotopes of their atoms such that the mass of $X^1$ differs from the mass of $X^2$; both Y are bonds cleavable under the same MS conditions as peptide bonds; and Z is a linker containing 1-20 linking members selected from C, N, O and S.

In some embodiments, in $X^1$ at least one linking member atom or at least one atom contained in a substituent of a linking member atom is a stable isotope different from the commonly found isotope of said atom and in $X^2$ all atoms are of said commonly found isotope. In some embodiments, both Y and/or both PBG are identical.

In some embodiments, Z in formula (1) is modified by further inclusion either of chemical moiety that permits enrichment of the crosslinked peptides or a functional group for attaching such chemical moiety. Further, in some embodiments, Z in formula (1) is modified by further inclusion of a substituent comprising a reporter ion whose intensity in the mass spectrum indicates the abundance of a crosslinked protein in a sample relative to its level in another sample(s). The crosslinked proteins from the different samples can be distinguished because they are labeled with isobaric tags which produce different reporter ions during MS2 analysis.

The invention is also directed to methods to identify and optionally quantitate interacting proteins using the linkers of formula (1).

BRIEF DESCRIPTION OF THE DRAWINGS

FIG. 1A shows the schematic of the linker itself FIG. 1B illustrates the coupled crosslinkers and the resultant cleavage products thereof. FIG. 1C shows the schematic mass spectra obtained as MS1 and MS2 from crosslinked peptides derived from the crosslinked proteins.

MODES OF CARRYING OUT THE INVENTION

Figure 1:
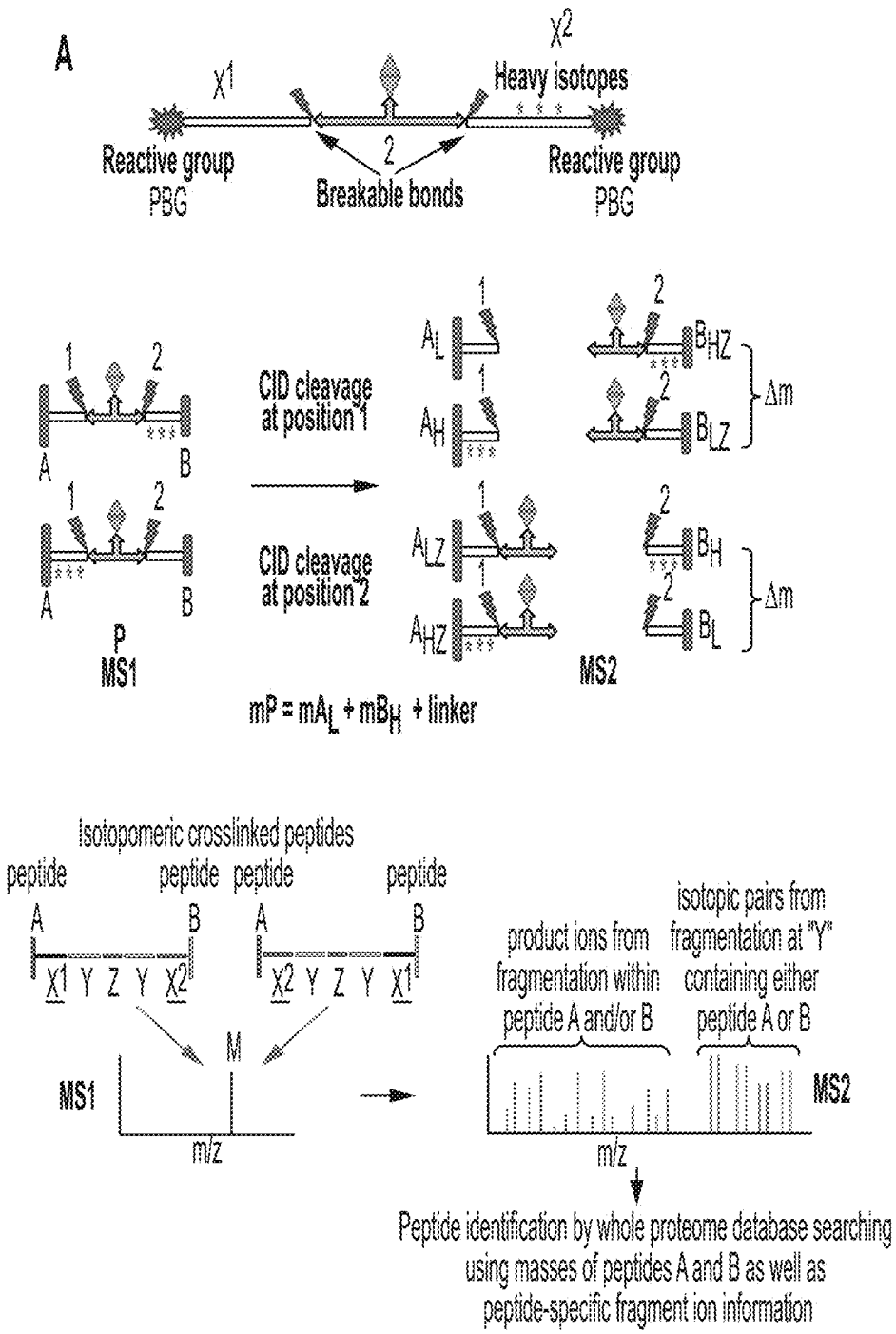
FIGS. 1A-1C show crosslinking molecules of the invention including an embodiment wherein chemical moiety designated in the drawing as an "Enrichment handle" is included.

The general features of the crosslinkers of one embodiment of the invention are illustrated in FIG. 1. As shown in FIG. 1A, the crosslinker has two "reactive groups", i.e., PBG in formula (1), at either end coupled to breakable bonds that bracket the linker Z which is shown as a substantial sequence, but can consist of only one linking atom. In the embodiment shown, the Z portion of the molecule contains an Enrichment handle). As also shown in FIG. 1A, the linker coupling one of the reactive groups to the breakable bond, $X^1$, contains only "normal" or commonly found isotopes of the atoms contained in it, whereas the second linker, labeled $X^2$, contains one or more, in this case, three, stable isotopes that are typically heavier than the normal isotope.

FIG. 1B shows the behavior of the crosslinker when coupled to peptides or proteins A and B. Since the reactive groups shown in this embodiment are identical, A and B are equally likely to be bound to either end of the molecule. Thus, approximately half of the molecules will have A bound through $X^1$ and B bound through $X^2$ and the opposite for the remaining half of the molecules. Also shown in FIG. 1B is the result of cleavage at the breakable bonds. As shown, if the crosslinker is cleaved at position 1, a doublet will arise for each of A and B wherein the molecular weight differs slightly because of the isotope content of $X^1$ vs. $X^2$. The doublets arise because of the roughly equal distribution of the portions of the crosslinker coupled to the protein. A second doublet containing peptide A and a second doublet compound B will also be obtained when the second bond is broken as shown.

As is understood in the art, although the crosslinker initially binds to specific residues in the interacting proteins, thus preserving their proximity, in order to conduct the mass spectrometric analysis, the sample is first treated with a protease that cleaves proteins at predictable cleavage sites to result in a mixture of crosslinked of peptides that represent only portions of the proteins originally crosslinked. Thus, prior to subjecting the sample to mass spectroscopy, the crosslinked proteins are subjected to treatment with a protease, such as trypsin, and the molecules actually subjected to mass spectrometry are crosslinked peptides.

In a typical experiment, MS1 shows only the mass/charge of the peptides linked through the crosslinker. Upon selection of the ion representing the crosslinked peptides themselves, and subjecting this ion to MS2 analysis, product ions are generated from fragmentation within the component peptides A and/or B and ions that appear as doublets are generated from fragmentation at each Y containing either peptide A or peptide B. Thus, MS2 results in four pairs of doublets depending on the location of the breaking bond— two pairs for each of the peptides, one pair of which comprises Z and the other pair of which does not.

FIG. 1C shows the schematic spectra that are generated from these peptides.

FIG. 1C shows this critical feature of the invention. In addition to the four pairs of doublets that occur in the MS2 spectrum, the fragmentation pattern for each of the peptides also appears because the cleavage reaction that breaks bonds at positions 1 and 2 also results in a fragmentation pattern resulting from breaking the peptide bonds in peptides derived from A and B. These do not occur, for example, in the MS2 spectrum of the Gunawardena document cited above. In order to obtain an MS2 spectrum with all the required information, therefore, the cleavable bonds, each Y, must be such that it is cleavable under the same dissociation conditions as the peptide bonds resulting in fragmentation of the peptides so that the information obtained, for example, by Gunawardena requiring both MS2 and MS3 spectra, is obtained simultaneously in the MS2 spectrum.

Thus, the bonds represented by Y may, but need not be, more labile than the peptide bonds contained in the peptides to which the crosslinker is coupled. The critical feature is that in the conduct of the mass spectrometry process, the dissociation method used to obtain MS2 is such that both the bonds represented by Y and the bonds broken to obtain the fragmentation pattern of the peptides are severed. There is a substantial number of dissociation reactions available in the art, including electron transfer disassociation (ETD), negative ion induced dissociation, high energy collision induced dissociation (HCD), low temperature plasma ionization (LTPI) and collision induced dissociation (CID). The dissociation method employed in the method of the invention is such that both Y bonds are dissociated as well as dissociation of the peptide bonds in the peptides.

One advantage of the crosslinkers of the invention is that the breakable bonds represented by Y may be asymmetric. This is advantageous because one readily apparent bond useable in the present case in a peptide bond itself. This is practical because there are two breakable bonds, whereas this would not be feasible if only a single cleavable bond were present, this because the peptide bond would destroy the symmetry of the two linking arms. It will be apparent as well that although it is advantageous from the standpoint of ease of design that both Y be identical, this is not required as long as the method provides consistent breakage of these bonds so that both are in effect broken in conjunction with obtaining MS2.

The bonds represented by Y, thus, need not be more labile than the peptide bonds in the peptides themselves. In order to obtain all of the required information in the MS2 spectrum, the dissociation of the moiety exiting the MS1 spectrum prior to MS2 should result in the fragmentation of the coupled peptides as well as cleavage of both Y. This is in contrast to the dithiol linkage of Gunawardena where the dithiol linkage only is cleaved in the transition between MS1 and MS2 leaving further dissociation to be displayed in MS3.

In addition, also not shown in FIG. 1 is one alternative embodiment wherein the two protein reactive groups are not identical. The lack of simplicity and symmetry when non-identical protein binding groups are employed can be overcome by utilizing an equimolar mixture of the crosslinkers. Thus, in effect, the symmetrical reactivity is restored by virtue of the overall equivalence of the crosslinking reactions. That is, by using an equimolar mixture of the crosslinkers both proteins A and B remain equally likely to bind the $X^1$ related end and the $X^2$ related end of the crosslinker. Thus, the pattern of doublets shown in FIG. 1 is still maintained.

Because the presence of the doublets in the spectrum is immediately discernible, the mass of the peptides can be determined from this parental peptide linked to the portion of crosslinker which it retains. The database search for a match to the accompanying fragmentation pattern can then be limited to peptides of this mass.

In fact, it is only needed to determine the mass of a doublet representing either peptide A or peptide B since the overall mass of the crosslinked peptides prior to cleavage is known and by subtracting the mass associated with the observed doublet the remaining mass of the unobserved peptide can be calculated. Knowing the exact masses of peptide A and peptide B (as determined by observing the doublet), a whole proteome database search is simplified as there is no need to consider all the peptide combinations that add up to the mass of an intact crosslinker precursor. This results in changing the quadratic increase of a combinatorial database search to a linear increase of database searches.

The chemical nature of the crosslinking molecules of the invention is varied and a large number of alternatives are included as long as the above parameters are observed. The protein reactive group can be any known functional group that is interactive with functional groups available on proteins such as sulfhydryl carboxyl or amino groups. Thus, the protein reactive groups may be halides, succinimides, substituted succinimides, or carboxylic acids or derivatives such as acyl halides or anhydrides. Those of skill in the art will understand what groups are commonly used for interaction with proteins.

The linking groups $X^1$ and $X^2$ are typically carbon chains optionally containing one or more heteroatoms and optionally substituents such as methyl groups or other inert branches. It is critical that the chemical structures of the linkers be symmetric and identical, but that they have different masses due to differences in isotope content. In the most simple embodiment, one of them contains only atoms that are in the form of the commonly encountered isotope, at least one atom is in a stable uncommonly encountered isotope in the other. Thus, one of the chains may contain all of its carbon atoms as $^{12}C$ and the other linker contain one or more $^{13}C$'s. One of the chains may have all of its hydrogen atoms in the typical form, but contain one or more deuterium atoms in the other. Alternatively, all of the oxygen in one chain may be $^{16}O$ while in the other one or more of said oxygens is $^{18}O$, or $^{14}N$ vs. $^{15}N$. The number of heavy isotope substitutions in, for example, $X^2$ as compared to $X^1$, is arbitrary; at least one such substitution must be made, but all of the corresponding atoms may be thus substituted or some intermediate number. Combinations of substitutions, for example, carbon 13 or deuterium or oxygen 18 may also be used. In theory, various combinations of such isotopes could be distributed among $X^1$ and $X^2$ as long as chemical identity is retained and there is a differential in the mass of the linkers. Thus, for example, $X^1$ might contain two deuterium substitutions while $X^2$ contains three $^{13}C$ and one $^{18}O$ substitution. However, preparation of the crosslinker is simplified if one of the linkers contains only commonly found isotopes and the other contains one or more of the corresponding heavy forms. The locations of any heavy isotopes within either of the linkers do not matter.

Suitable bonds represented by Y can include those that require relatively high energies to cleave. Such bonds include peptide bonds themselves as well as N—C bonds in general in which case, the linking member may be a single carbon or single nitrogen. It will be apparent to the skilled artisan the types of bonds permitted as embodiments of Y.

The chemical moiety, optionally further included in Z in one embodiment can be any convenient ligand such as biotin or other moiety that can be coupled, for example, to a binding partner on a solid support and used to separate the crosslinked proteins (or crosslinked peptides) from the remainder of the sample which separated crosslinked proteins (or peptides) can then be recovered from the solid support and subjected to the MS determination. Functional groups included in Z for coupling enrichment handles are also varied and depend on the particular design of the linkage to the enrichment handle. Selection of the enrichment handle is arbitrary and the method of linking the enrichment handle to the sequence represented by Z is also arbitrary. The linkage to the enrichment handle may be direct with respect to the linking atoms or heterobifunctional or homobifunctional linkers may be used. However, if complex moieties, e.g., affinity ligands, are included in Z, in some embodiments, linkers that are cleavable under conditions wherein Y remains stable are preferred so as to remove any complexity from the MS spectra that are introduced by the affinity ligand itself.

As will be further described below, in addition to, or in alternative to, further inclusion of a moiety that is suitable for binding or purification, the linking moiety Z may further include a reporter ion—i.e., a molecule of known mass whose quantitation in the mass spectral analysis can be employed to quantitate the relative levels of crosslinked proteins in two or more samples or to quantitate the level of a pair of crosslinked proteins in a single sample relative to a known concentration of added standard. This identifying reporter ion is of known mass and the peak representing this ion can readily be identified and the relative amounts of two such ions of different masses quantitated. These alternatives require a set of at least two crosslinkers wherein the reporter ion is included in a label that is isobaric among the members of the set.

Some typical crosslinkers within the scope of the invention are shown below:

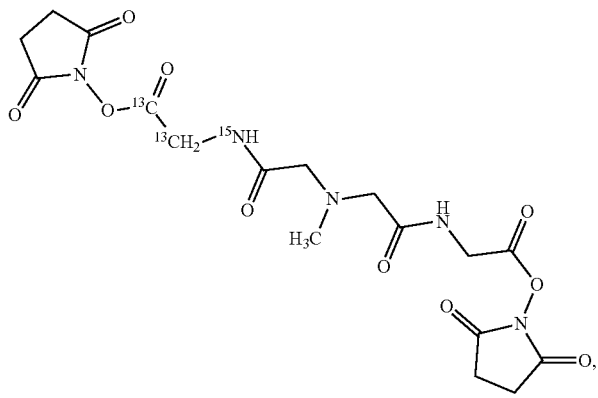

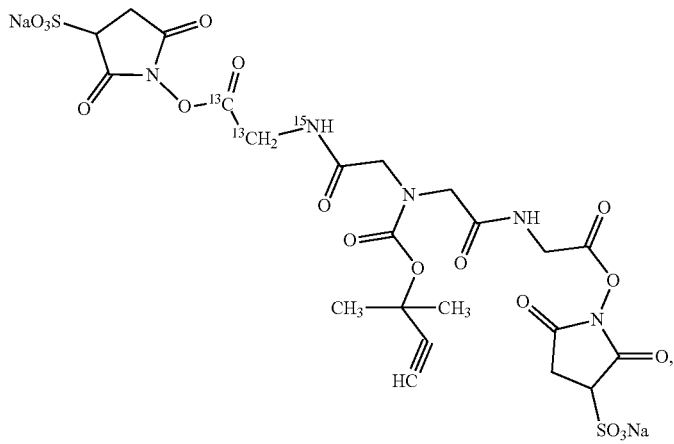

-continued
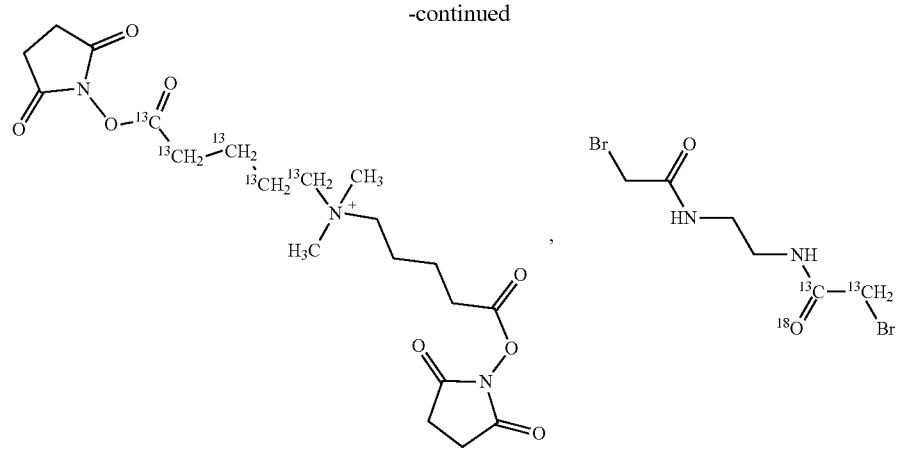
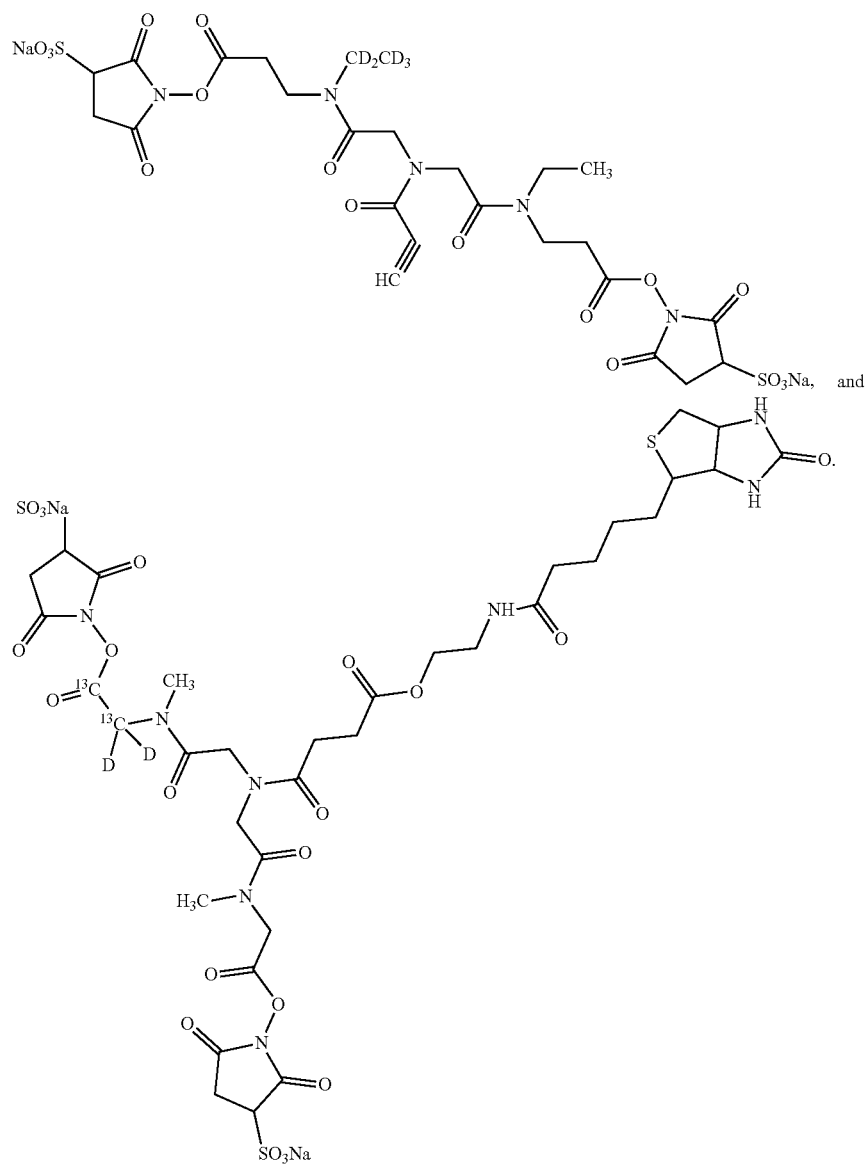
In the last structure shown above, the biotin included in the crosslinker is linked by a ester bond to the remainder of the molecule which bond can be cleaved by addition of hydroxylamine allowing specific and efficient release from, for example, streptavidin-containing beads that can be used in purification taking advantage of specific streptavidin-biotin binding.

Further embodiments that provide multiplex analysis of the relative quantities of crosslinked proteins in multiple samples. This requires a set of at least two crosslinkers with reporter ions of different molecular weights contained in labels that are isobaric among members of the set. Illustrative sets of crosslinker are shown below wherein R represents an isobaric label containing reporter ions of slightly differing mass thus allowing determination of the relative quantities of, in this illustrative case, crosslinked proteins derived from four different samples. The quantification method is basically that of Ross, et al. *Mol. Cell. Proteomics* (2004) supra, the contents of which are incorporated herein by reference. This method applied to the MS1 and MS2 spectra in a multiplexing format is illustrated by the cross-linking molecules shown below.

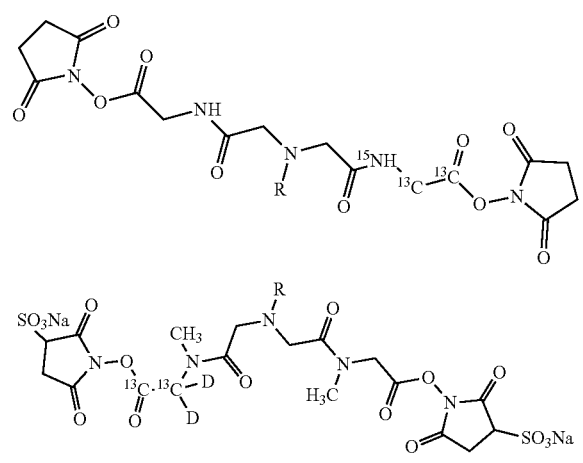

wherein R is

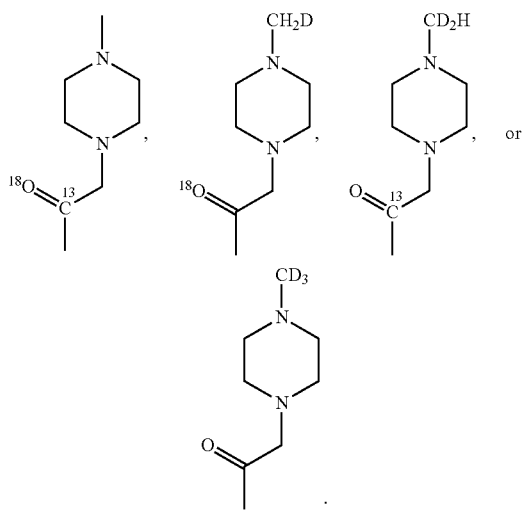

Crosslinkers shown can thus be provided as a set of four members, each with a different embodiment of R as an isobaric label as shown in the table below.

| R | Reporter ions | Mass |
|---|---|---|
| (piperazine with CH₃, ¹⁸O, ¹³C) | (piperazinium with CH₃) | 113.1079 |
| CH₂D (piperazine with ¹⁸O, ¹³C) | CH₂D (piperazinium) | 114.1131 |
| CD₂H (piperazine with ¹³C) | CD₂H (piperazinium) | 115.1184 |
| CD₃ (piperazine) | CD₃ (piperazinium) | 116.1237 |

As shown, the various embodiments of R are isobaric because the differing molecular masses of the reporter ions are counterbalanced by the moieties binding them to the linker itself. The reporter ions have slightly different masses and thus can readily be distinguished in the mass spectrum.

Thus, the MS1 spectra are undisturbed in their complexity since the embodiments of R are isobaric. However, in MS2, a series of reporter ions representing the levels of the crosslinked proteins coupled by each member of the set are present and readily identifiable due to their different masses and their relative amounts can thus be determined and the same MS2 spectra can be used both for identification and relative quantitation of the crosslinked peptides. MS2 fragmentation occurring at Y and within the linked peptides will generate the fragment ions for identification of the linked peptides as described above, and at the same time MS2 fragmentation occurring at the isobaric labels will generate specific reporter ions with masses that differ and thus can be identified by their m/z's and quantified by their intensities. These crosslinkers can therefore be used to study conformational changes in proteins and changes in protein-protein interactions in samples prepared under different conditions.

In the illustration above, four members of the set are compared, however, by appropriate design of the chemical nature of R, sets with larger numbers of members can be included, so that, for example, 5 or 6 or more samples can be analyzed.

In more detail, this method to quantitate the relative amounts of specifically interacting proteins in a multiplicity of samples (employing a set of crosslinkers of formula (1) wherein Z in each member of the set further comprises an isobaric label containing a reporter ion unique to said member of the set) comprises:

(a) contacting each sample comprising proteins with a member of a set of said crosslinkers to obtain crosslinked proteins in each sample;

(b) combining the samples and treating with protease to obtain crosslinked peptides;

(c) subjecting said crosslinked peptides to mass spectrometry under conditions wherein said crosslinked peptides remain substantially intact to obtain MS1;

(d) dissociating said crosslinked peptides under conditions wherein the bonds represented by Y, the peptide bonds within the peptides, and the bonds linking the reporter ion to the crosslinker are cleaved to obtain a mixture comprising peptide fragments and portions of the crosslinker coupled to said fragments or peptides and said reporter ion;

(e) subjecting the mixture in (d) to MS to obtain MS2;

(f) identifying doublets in said MS2 spectrum as representative of parent peptides of the fragmented portions thereof to ascertain the mass of the parent peptide;

(g) based on the doublets in (f), analyzing a protein sequence database with a database search algorithm to identify peptides of the appropriate mass that produce theoretical fragmentation patterns that correspond to the acquired MS2 fragmentation pattern; and (h) based on the level of reporter ions in (e), quantifying the relative abundance of crosslinked protein.

In some embodiments, the amount of pair of crosslinked proteins in a single sample can be determined by comparison with an added known concentration a standard pair of crosslinked peptides or proteins. The standard pair is crosslinked with a different member of a set of crosslinkers and the relative intensity of the peak of its reporter ion in MS2 permits determination of the amount of an unknown pair.

The following examples are offered to illustrate but not to limit the invention.

Preparation A

Preparation of Yeast RNA Polymerase II

An RPB1 (the largest subunit of RNA Polymerase (Pol) II) TAP tagged yeast strain was grown in 6×2 liters of YPD (20 g peptone, 30 g dextrose, 10 g yeast extract+0.002% adenine sulfate per liter) overnight. Cells were pelleted and washed with ice cold water and frozen into pellets in liquid nitrogen. The frozen pellets were ground in liquid nitrogen to a fine powder. The cell powder was then suspended in TEV extract buffer (TEB) [TEB: 20 mM Hepes, pH 7.6, 500 mM KOAc, 1 mM MgOAc, 1 mM EDTA, 20% glycerol, and protease inhibitors (PIs: 1 mM phenylmethylsulfonyl fluoride, 2 mM benzamidine, 3 µM leupeptin, 1 µM pepstatin A and 3.3 µM chymostatin)].

Cell lysates were then spun at 20 K×g for 20 minutes at 4° C. The supernatant was transferred to a new tube and spun again at 100 K×g for 90 minutes at 4° C.

Four hundred (400) µl IgG Sepharose™ beads (GE Life Sciences, Pittsburgh, PA) equilibrated with TEB, was added to the lysate and the mixture was incubated overnight at 4° C. with rocking. The beads were then batched washed with 200 mL TEB, followed by 50 mL TEV cleavage buffer (20 mM Hepes, pH 7.6, 200 mM KOAc, 1 mM EDTA, 0.1% NP-40, 20% glycerol, and PIs). The beads were then incubated in 6 mL of TEV cleavage buffer containing 75 µL of TEV protease (10 units/µL, Life Technologies, Carlsbad, CA) at 25° C. for 30 minutes, and then overnight at 4° C. The eluate was removed and the beads were rinsed by addition of 6 ml TEV cleavage buffer with rocking at 4° C. for 10 minutes.

Eluates were combined, 3× volume of calmodulin binding buffer (CBB) (CBB; 20 mM Hepes pH 7.6, 250 mM KOAc, 1 mM DTT, 1 mM MgOAc, 1 mM imidazole, 2 mM $CaCl_2$), 10% glycerol, 0.1% NP-40, and PIs) was added to sample, and the $CaCl_2$) concentration was adjusted to 3 mM. The sample was incubated with 3 mL Calmodulin Sepharose™ beads (Agilent technologies, Santa Clara, CA) equilibrated in the CBB, overnight at 4° C. The beads were washed with CBB containing 0.1% NP-40, and the bound proteins were eluted in 1 fractions with Calmodulin elution buffer (20 mM Hepes pH 7.6, 250 mM KOAc, 1 mM DTT, 1 mM MgOAc, 1 mM imidazole, 3 mM EGTA, 10% glycerol, 0.01% NP-40). Aliquots were analyzed by SDS-PAGE followed by Western blotting and silver staining.

Fractions containing RNA Pol II were combined and then concentrated using Centricon® YM-10 concentrators (Millipore, Billerica, MA).

Example 1

Synthesis of Crosslinker 5

The reaction sequence for this Example is as follows:

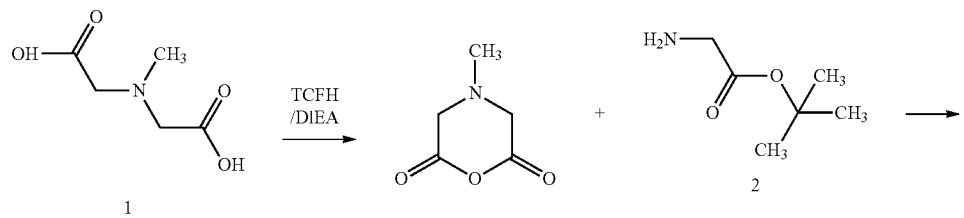

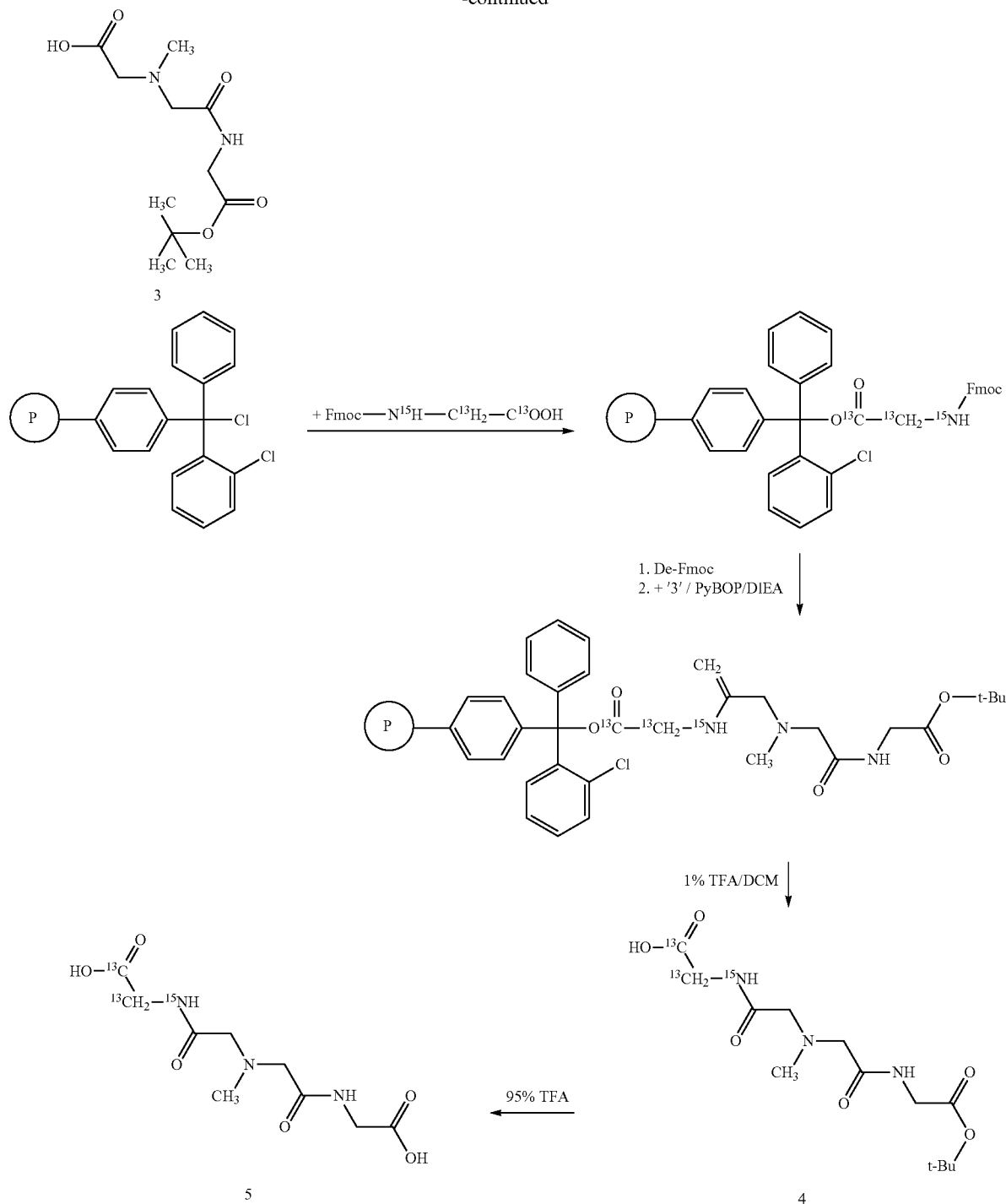

A mixture of methylimino diacetic acid (1) (1 eq), chloro-N,N,N',N',N'',N''-Tetramethylformamidinium hexafluorophosphate (TCFH) (1 eq), and N,N-diisopropylethylamine (DIEA) (2 eq) in dry DMF was stirred for one hour at room temperature. A solution of glycine tert-butyl ester (2) (1 eq) and DIEA (1 eq) in DMF was added to the mixture and stirred overnight to obtain product (3).

N-Fmoc-Gly-OH ($^{13}C_2$, $^{15}N$) shown circled in the scheme is loaded onto a 2-chloro trityl chloride resin (2 eq) in DMF with DIEA (4 eq) and the Fmoc protection is removed. A solution of 3 (3 eq) is added directly to the resin with (benzotriazol-1-yloxy)tripyrrolidinophosphonium hexafluorophosphate (PyBOP) (3 eq) and 1-hydroxybenzotriazole (HBot) (3 eq) under nitrogen bubbling for 3 hours. The resin was washed extensively with DMF/Methanol/DCM and 1% TFA/DCM is used to release the product from the resin. Cleavage solution was evaporated under the vacuum to get the sticky and oily product, which was dissolved in water and precipitated by ether to get the white powder of product 4. Ninety-five percent (95%) TFA/water is added to the product 4 to remove the tert-butyl protection group. Ether was then added to precipitate the final product 5 as white powder. The free acid of the final product 5 (100 mM) was activated using N,N,N'N,NpTetramethyl-O—(N-succinimidyl)uronium tetrafluoroborate (TSTU) (2 eq) and DIEA (6 eq) in DMF for one hour.
Example 2
Synthesis of Des-thio-biotinylated Crosslinker
The reaction scheme for this synthesis is as follows:
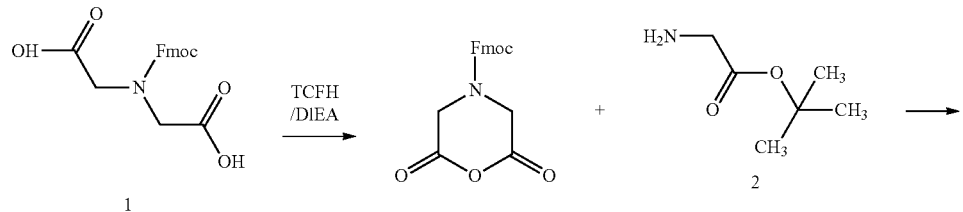
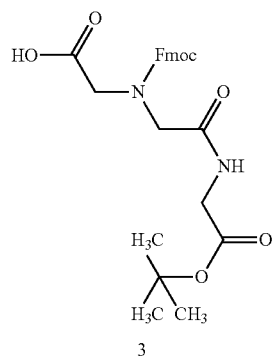
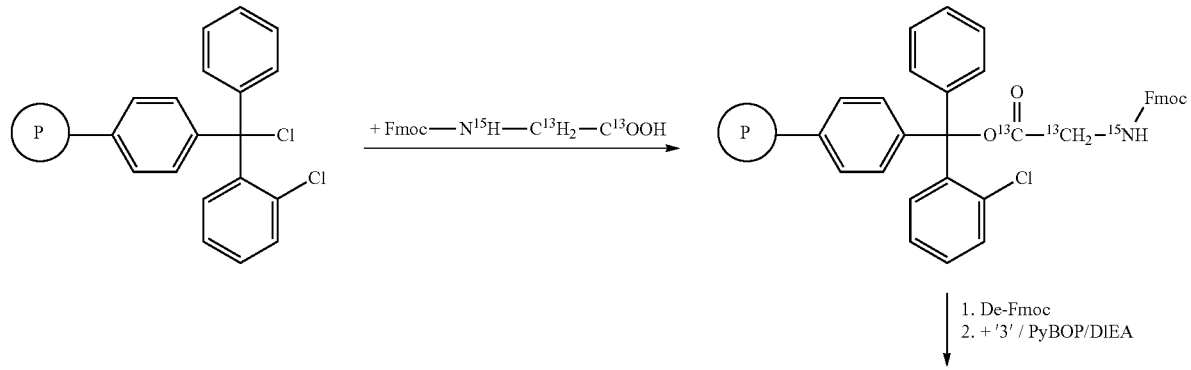
1. De-Fmoc
2. + '3' / PyBOP/DIEA
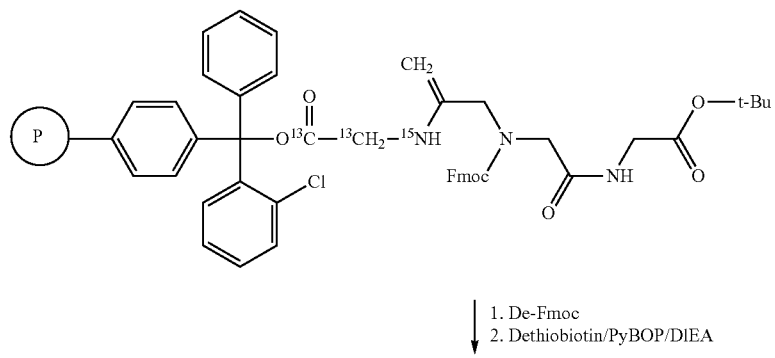
1. De-Fmoc
2. Dethiobiotin/PyBOP/DIEA

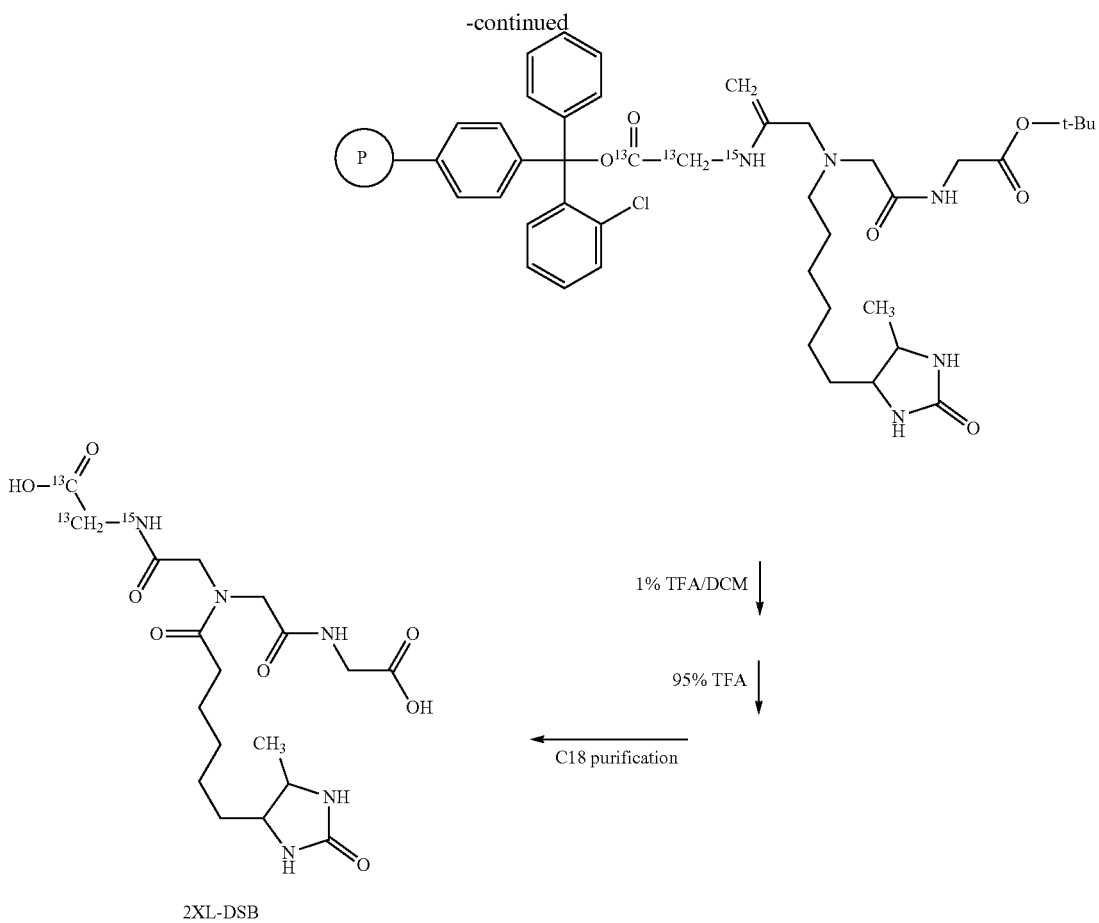

2XL-DSB

As shown, the synthesis is similar to that of the crosslinker of formula (5) shown in Example 1 except that des-thio-biotin is added as shown according to standard Fmoc peptide synthesis procedures. As above in Example 1, the resulting des-biotinylated crosslinker is further purified by C18 the reverse phase HPLC to obtain the pure acid form which can be activated by TSTU.

Example 3

MS Analysis of a Monolinked Peptide

This example demonstrates that the expected doublets appear in MS2 for a peptide that is coupled to the crosslinker of the invention.

The synthetic peptide acSDERIAKIGGLNDPRITVKEVQFGLFSPEEVR (SEQ ID NO: 1) (MW 1040.5752) is treated with the crosslinker of formula (5) of Example 1, which contains two carbons as $C^{13}$ and one nitrogen as $N^{15}$ in $X^1$. The protein-binding groups are both carboxyl ions and are coupled to the above peptide through the N-terminal amines of the lysine residues. The peptide was reacted with the crosslinker of formula (5) in PBS buffer, trypsin digested and cleaned by C18 reverse phase HPLC. Thus, the monolinked peptide resulting from trypsin digestion, AK[374.18] IGGLNDPR (SEQ ID NO: 2), was isolated. The molecular weight of the compound of formula (5) plus the mass of Lysine is inserted in brackets in the sequence. The MS2 spectrum was determined for the isolated monolinked peptide using an Orbitrap™ Elite Fourier Transform Mass Spectrometry (FTMS) with 1 FTMS1/10 FTMSn, HCD normalized energy 35%.

Figure 2:
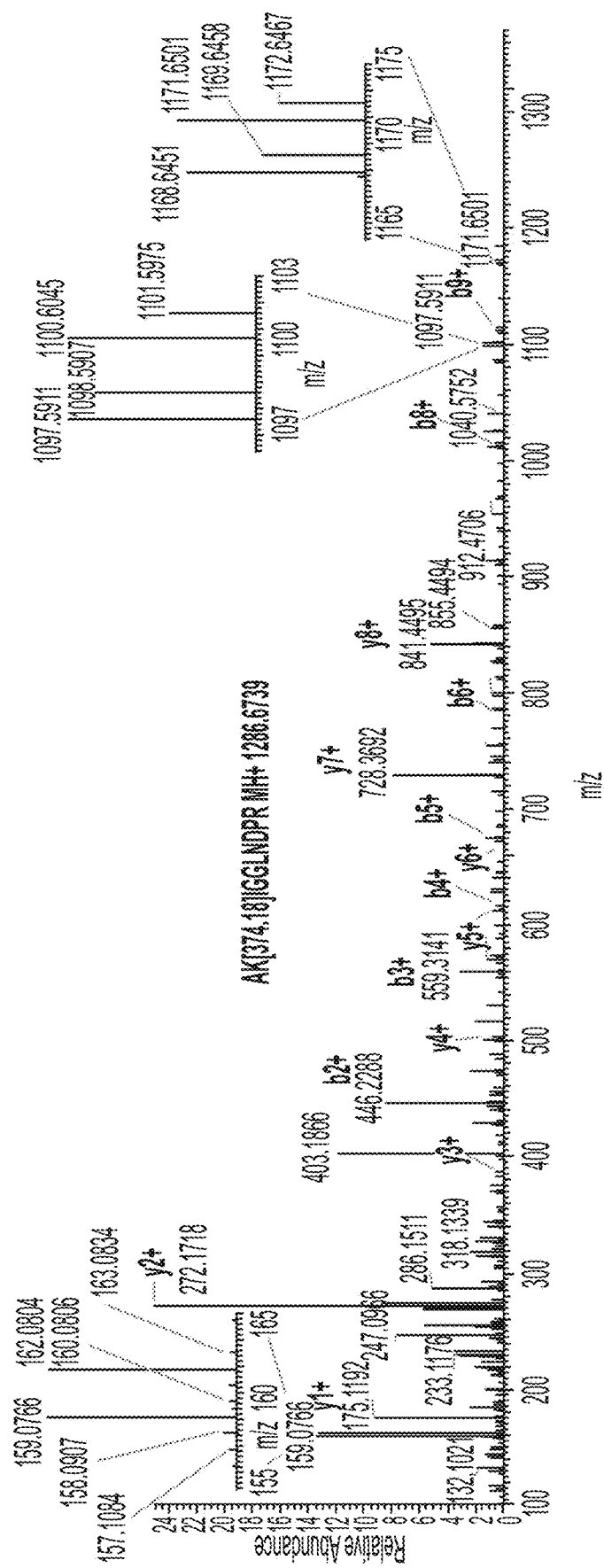
FIG. 2 shows the MS2 spectrum of a monolinked peptide (AK[374.18]IGGLNDPR (SEQ ID NO: 2)); that is a peptide that has been modified by reaction with one of the reactive groups of the crosslinker of the invention and structures of the fragments associated with this spectrum.
Figure 2:
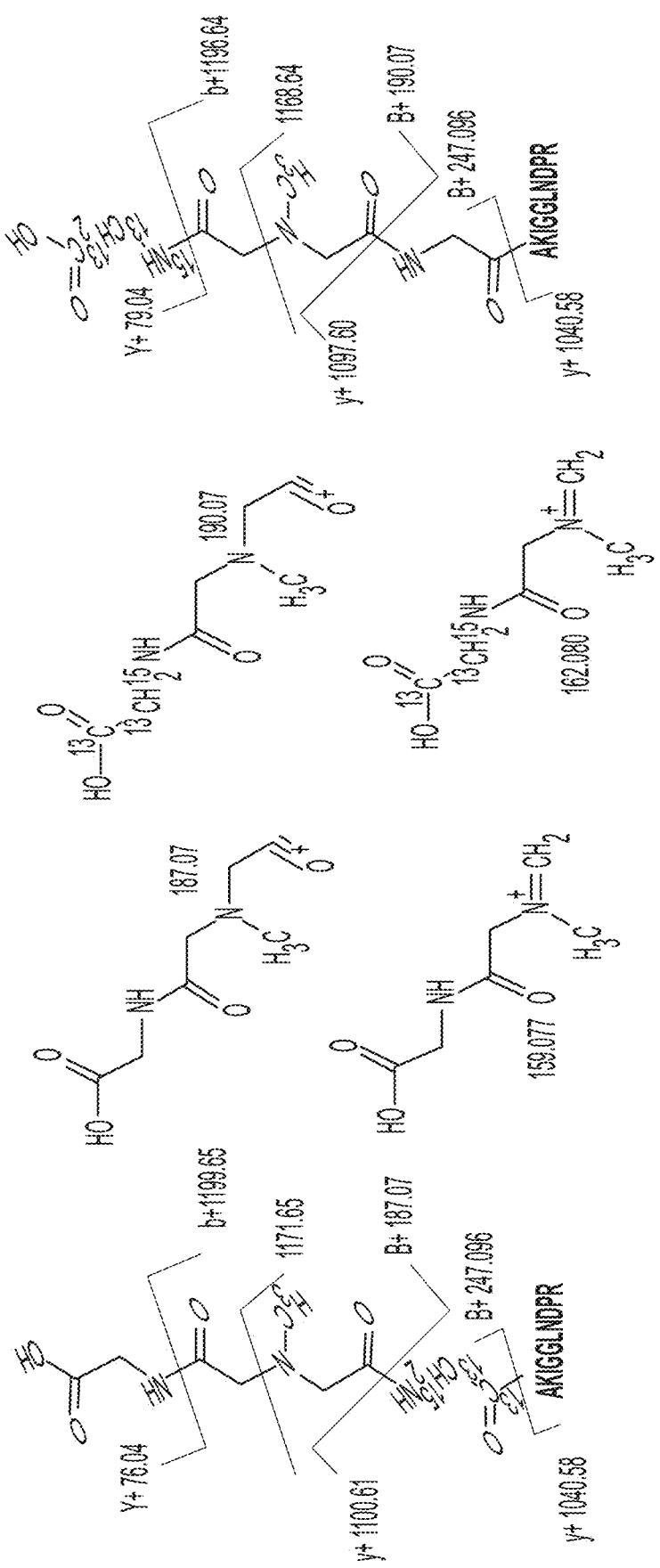

FIG. 2 shows the MS2 spectrum. Two isotopic doublets corresponding to the two breakage bonds in the crosslinker are shown in the enlarged inserts (1097.5911 and 1100.6045 in one doublet, 1168.6451 and 1171.6501 in the other). The doublet ions have similar intensities as expected. The pair of 1097.5911 and 1100.6045 is a y ion pair due to modification of the peptide by the glycine moiety contained in the crosslinker (with modification masses of 57.0214 and 60.0244). The pair of 1168.6451 and 1171.6501 at lesser intensities is an unusual breakage at the amine which gives a modification mass of 128.0586 and 131.0616 to the naked peptide ion. The b ion doublet of 1196.94 and 1199.65 was not observed. A unique doublet of 159.0766 and 162.0894 represents either a ions or b ions after neutral loss of CO from the free end of the crosslinker. This unique ion pair is a characteristic feature for monolinks of the crosslinker of Formula (5).

Example 4

MS2 of Crosslinked Peptides

A sample containing only the crosslinked peptides that would be generated from trypsin digestion of the peptide linked in Example 2 AKIGGLNDPR (SEQ ID NO: 2) and TVKEVQFGLFSPEEVR (SEQ ID NO: 3) was isolated and subjected to mass spectrometry in a manner described in Example 3.

Figure 3:
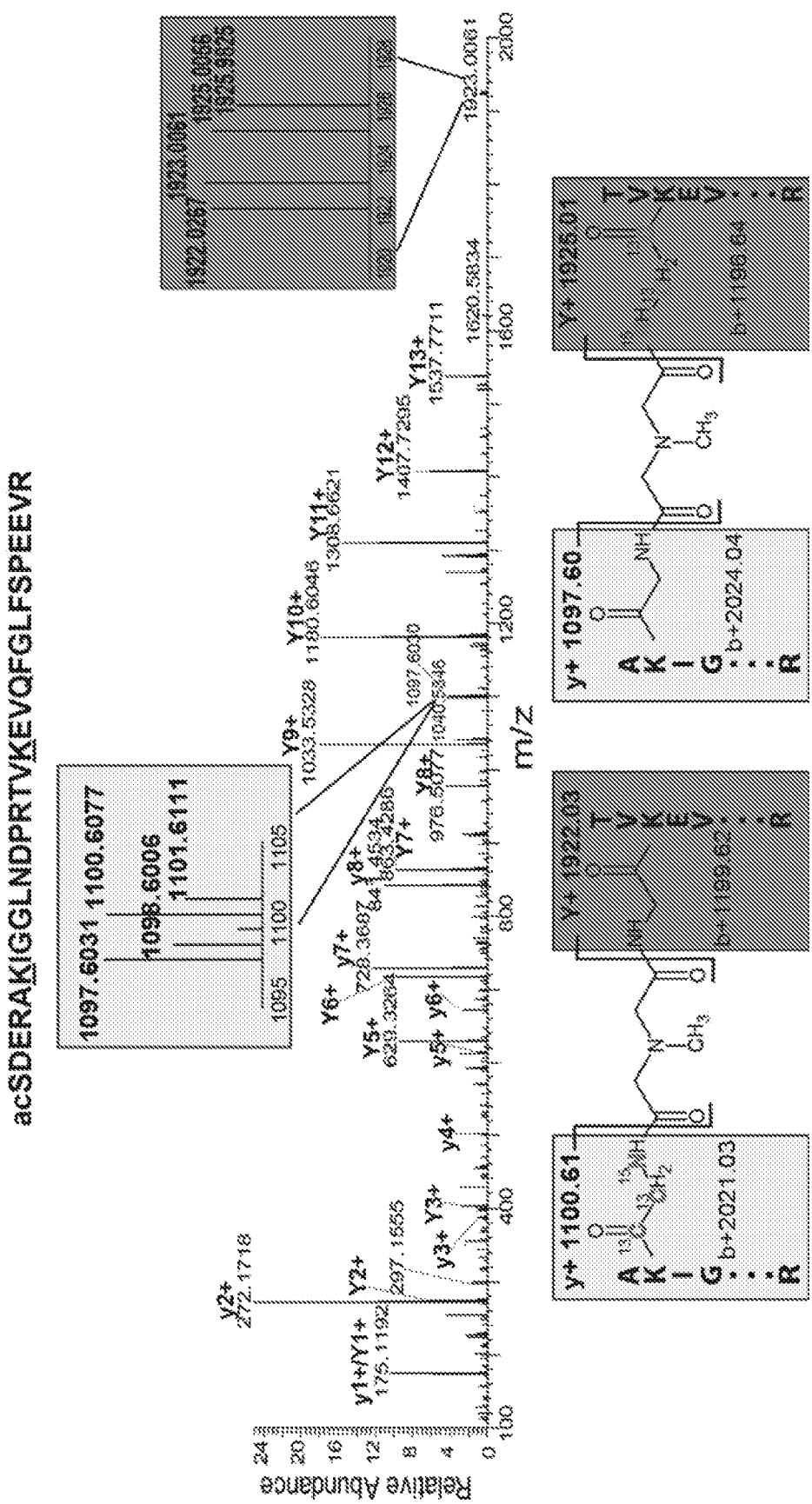
FIG. 3 shows the MS2 spectrum for a crosslinked molecule (acSDERIAKIGGLNDPRITVKEVQFGLFSPEEVR (SEQ ID NO: 1)) comprised of two peptide of different sequences (AKIGGLNDPR (SEQ ID NO: 2) and TVKEVQFGLFSPEEVR (SEQ ID NO: 3)).

The spectrum of these crosslinked peptides is shown in FIG. 3. The y ions corresponding to the peptide AKIG- GLNDPR (SEQ ID NO: 2) are shown as lower case 'y's. The y ions corresponding to peptide TVKEVQFGLFSPEEVR (SEQ ID NO: 3) are shown as upper case 'Y's. Two doublets of 1097.6031 with 1100.6077 and 1922.0267 with 1925.0056, corresponding to the y ions of the peptide AKIGGLNDPR (SEQ ID NO: 2) plus a glycine modification and peptide TVKEVQFGLFSPEEVR (SEQ ID NO: 3) plus a glycine modification respectively, are shown in the enlarged inserts. The y-ion pairs are distinguishable from other ions by their appearance as doublets of ~equal intensity and a mass difference of 3.0 Da. The actual appearance of the doublets is shown above the spectrum. The 1922.0267/1925.0056 doublet and the 1097.6031 and 1100.6077 doublet represent each of the peptides respectively—one member of the doublet comprising the $C^{13} N^{15}$ labeled glycine and the other the non-labeled glycine derived from cleavage of the crosslinker of formula (5). Since the two peptides are from the yeast RPB1 sequence, the whole yeast proteome with contaminants (6876 entries) was searched along with its reverse decoy sequences using the in-house developed Nexus algorithm. The search was completed within 30 min and two crosslinks were correctly identified from this synthetic peptide as shown in Table 1. The numbers in the brackets are the total mass of the other crosslinked peptide plus the crosslinker and the lysine residue mass. The period symbol indicates where trypsin cleavage occurred.

Only one search result was incorrect. Careful examination of the spectrum used for this identification indicates that it was produced by fragmentation of peptide TVKEVQFGLFSPEEVR (SEQ ID NO: 3) crosslinked to N-terminal deaminated peptide AKIGGLNDPR (SEQ ID NO: 2).

crosslinked peptides were purified on a C18 reverse phase HPLC column and fractionated using a microcapillary strong cation exchange column.

Peptides were analyzed by MS on a Thermo Scientific Orbitrap™ Velos with HCD fragmentation. The resulting MS2 was searched against a yeast whole proteome database with reverse decoy sequences using an in-house developed *Nexus* search algorithm. False discovery rate (FDR) was estimated based on identifications containing peptides from the reverse decoy sequences, and sensitivity was calculated based on a limited database search using a database containing only Pol II subunit protein sequences.

Figure 4A:
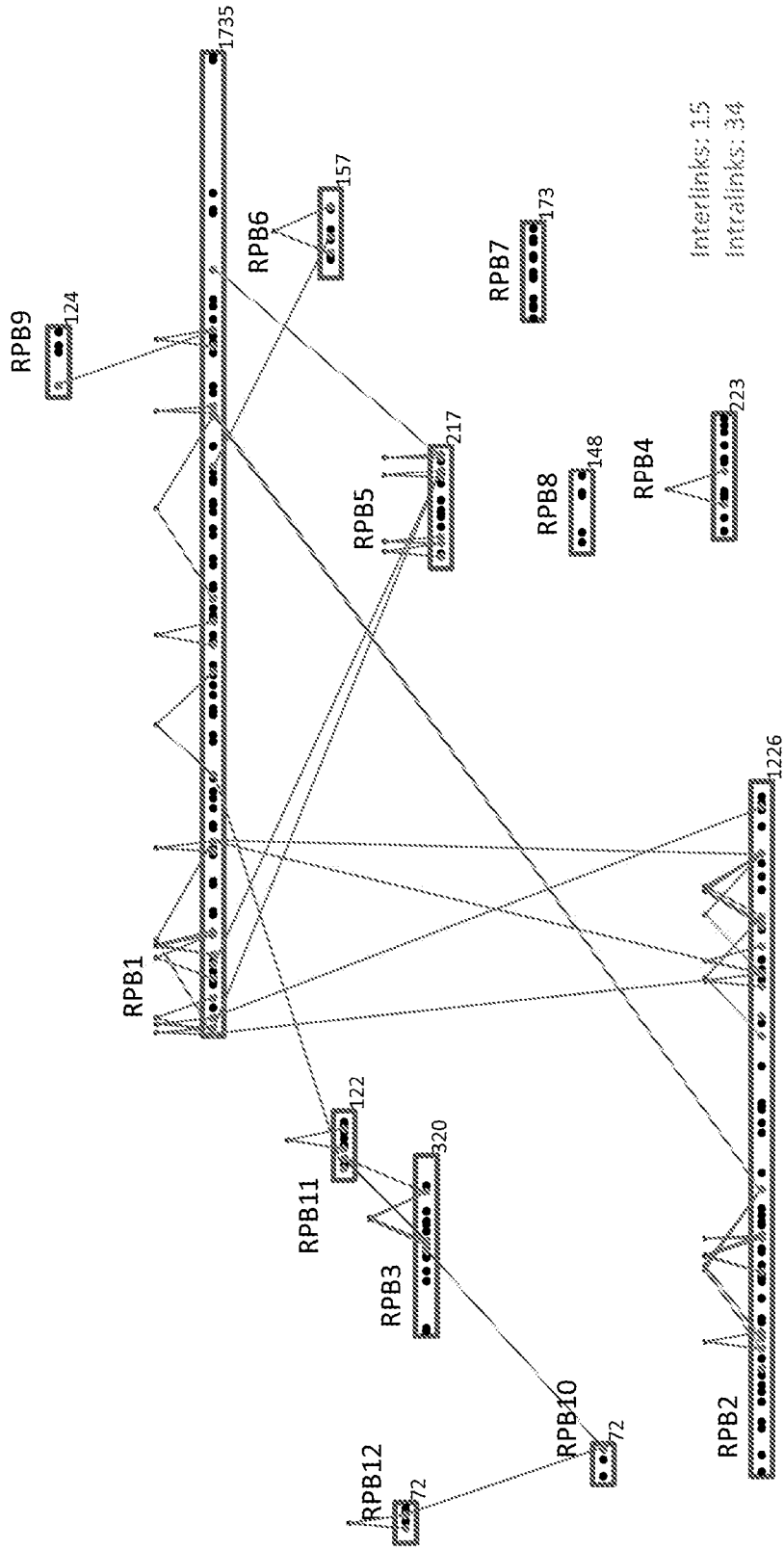
FIG. 4A shows the location of identified interlinks between RNA polymerase II subunits of Example 5 and the intralinks within a Pol II subunit.
Figure 4B:
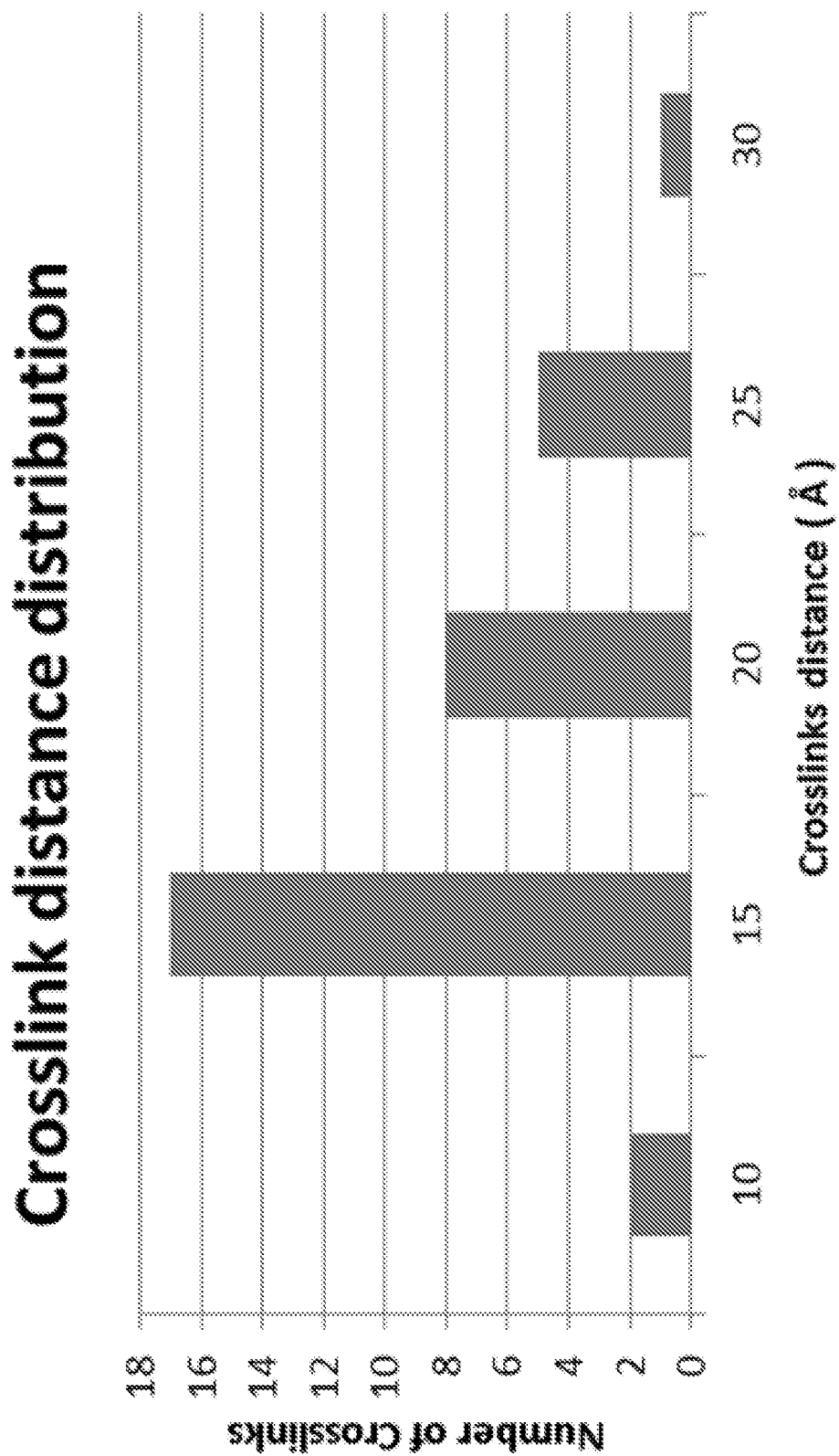
FIG. 4B shows the alpha carbon (Ca) distance between crosslinked lysine residues.

At 1.1% FDR and 70% sensitivity, 84 spectra corresponding to crosslinked peptides between Pol II subunits were identified by searching the yeast proteome database with reverse decoy sequences (total of 13,600 entries) in less than 1 hour. These crosslinks include 15 interlinks (between Pol II subunits) and 34 intralinks (within a Pol II subunit) as shown in FIG. 4A. These crosslinks were mapped onto the Pol II crystal structure 1WCM.pdb and the alpha carbon (Cα) distance between crosslinked lysine residues was measured. As shown in FIG. 4B, Ca distances were between 7 to 27 Å which are all less than the theoretical Cα crosslinking distance of 32-37 Å for the crosslinker of Formula 5. The theoretical linker distance of the crosslinker of Formula 5 is about 15 Å.

Example 6

Crosslinking Analysis of Bovine Serum Albumin

The DSB labeled crosslinker of Example 2 was used to crosslink BSA using the procedure described in Example 3. After trypsin digestion, the crosslinker-modified peptides

TABLE 1

| Peptide 1 | protein1 | peptide 2 | protein2 | number of spectra |
|---|---|---|---|---|
| R.TVK[1395.75]EVQFGLFSPEEVR.A | YDL140C | R.AK[2220.15]IGGLNDPR.L | YDL140C | 78 |
| R.AK[1395.75]IGGLNDPR.L | YDL140C | R.AK[1395.75]IGGLNDPR.L | YDL140C | 21 |
| R.TVK[1381.74]EVQFGLFSPEEVR.A | YDL140C | K.K[2220.15]LGNDHSKK.W | YLR020C | 1 |

[Sequences listed in Table 1, under Peptide 1 in order: SEQ ID NO: 3, SEQ ID NO: 2, SEQ ID NO: 3; under Peptide 2 in order: SEQ ID NO: 2, SEQ ID NO: 2, SEQ ID NO: 4]

Example 5

Crosslinking Analysis of the RNA Pol II Complex-Crosslinker of Formula 5

TSTU (N,N,N',N'-tetramethyl-O—(N-succinimidyl)uronium tetrafluoroborate, Sigma) activated crosslinker of Formula 5 was added to the purified RNA Pol II to a final concentration of 5 mM and the reaction was allowed to proceed at RT for 2 hours before adding ammonium bicarbonate to a final concentration of 20 mM to quench the reaction. The crosslinked sample was precipitated using trichloroacetic acid, reduced, alkylated by iodoacetamide and trypsin digested overnight. After trypsin digestion, the were first affinity enriched on a StrepTactin® agarose column (Novagen) through the desthiobiotin enrichment handle on the crosslinker, and then analyzed on the Elite Orbitrap™. The MS2 spectra were searched against a bovine database (9,396 entries) and its reverse decoy database using the Nexus searching algorithm. Identifications assigned to non-BSA peptides and decoy sequences were used to estimate the false discovery rate (FDR), and results from a search against a database containing only BSA sequences (P02769 and Q3SZR2) were used to estimate the sensitivity. At less than 1% FDR and around 68% sensitivity, 84 spectra corresponding to 23 crosslinked peptides from BSA protein were identified. These are shown in Table 2.

TABLE 2

| index | Crosslinked peptides | CA distance(Å) |
|---|---|---|
| 1 | K*VPQVSPLVEVSR(413)---HKPK*AEEQLK(537) | 11.36 |
| 2 | GACLLPK*IEMR(180)---EK*VLSSAR(187) | 10.97 |
| 3 | CCK*PESER(431)---SLGK*VGR(439) | 13.51 |
| 4 | LFFHADICLPDEK*QIK(520)---K*QALVELLK(524) | 6.42 |
| 5 | NYQEAK*DAFLGSFLYEYSR(322)---LAK*EYEALEECCAK(350) | 11.98 |
| 6 | NYQEAK*DAFLGSFLYEYSR(211)---ALK*AWSVAR(322) | 13.99 |
| 7 | VHK*ECCHGDLLECADDRADLAK(211)---ALK*AWSVAR(242) | 9.73 |
| 8 | LAK*EYEALEECCAK(211)---ALK*AWSVAR(350) | 13.54 |
| 9 | LVDLK*VHK(211)---ALK*AWSVAR(239) | 8.96 |
| 10 | AEFVEVK*LVDLK(211)---ALK*AWSVAR(232) | 11.02 |
| 11 | CCK*PESER(221)---LSQK*FPK(439) | 20.54 |
| 12 | RHPYFYAPELLYYANK*YNGVFQECCQAEDK(159)---EK*VLSSAR(187) | 11.53 |
| 13 | LAK*EYEALEECCAK(350)---VK*CCESLVNR(474) | 17.99 |
| 14 | FK*DLGEEHFK(4)---DHK*SEIAHR(12) | 13.38 |
| 15 | LKECCDK*PLLEK(187)---EK*VLSSAR(280) | 20.04 |
| 16 | EK*VLSSAR(187)---LSQK*FPK(221) | 20.3 |
| 17 | EK*VLSSAR(187)---SLGK*VGR(431) | 13.69 |
| 18 | CCK*PESER(187)---EK*VLSSAR(439) | 18.22 |
| 19 | CASIQK*FGER(204)---ALK*AWSVAR(211) | 13.47 |
| 20 | VK*CCESLVNR(204)---CASIQK*FGER(474) | 13.14 |
| 21 | LAK*EYEALEECCAK(204)---CASIQK*FGER(350) | 16.43 |
| 22 | LCVLHEK*PVSEK(204)---CASIQK*FGER(465) | 13.24 |
| 23 | AEEQLK*VMENFVAFVDK(524)---K*QALVELLK(544) | 14.33 |

[Sequences listed in Table 2: index 1-23 represent SEQ ID NOS; 5-27, respectively]
Distances between alpha carbons of crosslinked lysines (Cα distance) were measured using 4F5S.pdb.
The asterisk indicates the crosslinked lysine residues.
The numbers in parentheses indicate the position of the preceding amino acid in the BSA sequence.

For all 23 crosslinked peptides, the alpha carbon distances between the crosslinked lysine residues in the crystal structure (4F5S.pdb) are all within the theoretical crosslinking distance for the crosslinker.

The invention claimed is:

1. A crosslinker for identifying specifically interacting proteins and the sites of crosslinking by mass spectrometry (MS) which crosslinker has the formula (1):

PBG-$X^1$—Y—Z—Y—$X^2$-PBG　　(1)

wherein each protein binding group (PBG) reacts with an amino, sulfhydryl, hydroxyl or carboxyl group;
$X^1$ and $X^2$ are structurally identical linkers containing 3-15 linking member atoms selected from C, N, O and S, and wherein $X^1$ and $X^2$ contain different isotopes such that the mass of $X^1$ differs from the mass of $X^2$;
both Y are bonds cleavable under the same MS conditions as peptide bonds; and
Z is a linker containing 1-20 linking members selected from C, N, O and S.

2. The crosslinker of claim 1 wherein in $X^1$ at least one linking member atom or at least one atom contained in a substituent of a linking member atom is a stable isotope different from the commonly found isotope of said atom and in $X^2$ all atoms are of said commonly found isotope; and/or the PBG are identical; and/or both Y bonds are identical.

3. The crosslinker of claim 1 wherein Z further comprises a chemical moiety for enrichment of the crosslinked peptides or a functional group for binding said chemical moiety.

4. The crosslinker of claim 2 wherein said at least one stable isotope different from the commonly found isotope is $^{13}C$, $^2H$, $^{15}N$ or $^{18}O$.

5. The crosslinker of claim 1 wherein both Y are N—C bonds.

6. The crosslinker of claim 5 wherein both Y are peptide bonds.

7. The crosslinker of claim 1 wherein the PBG groups are halide, aldehyde, carbonates or hydroxysuccinimide ester groups.
8. The crosslinker of claim 1 selected from the group consisting of
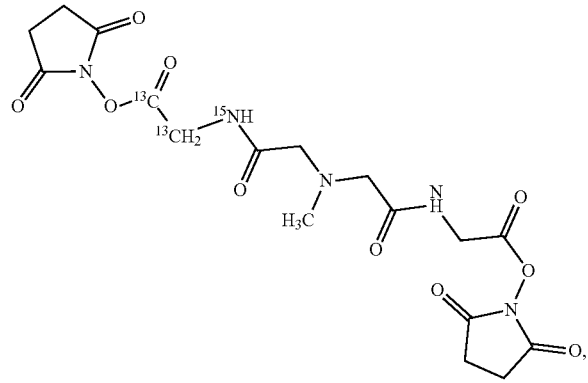
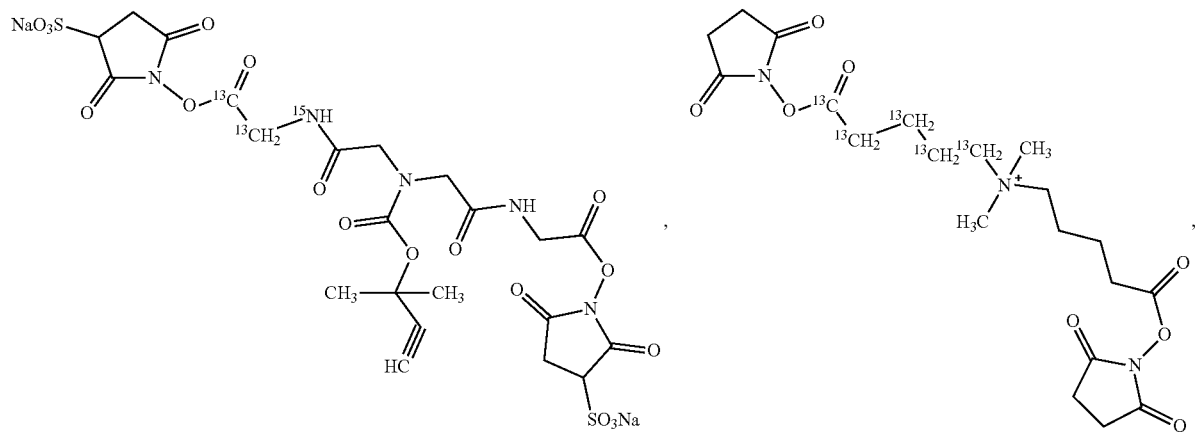
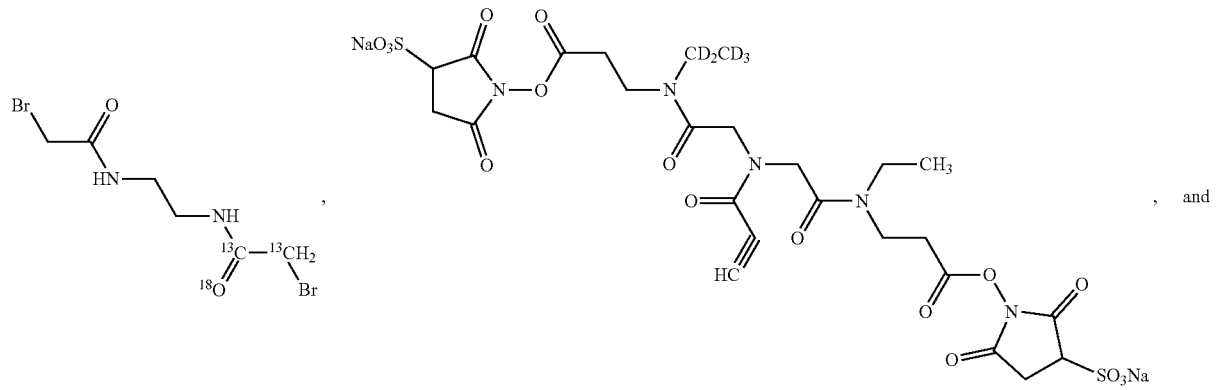

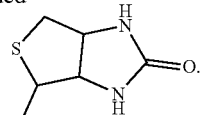

-continued

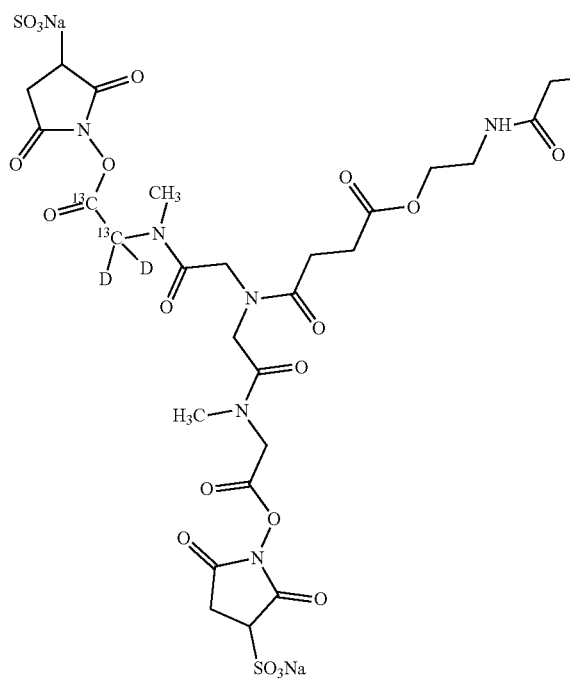

9. The crosslinker of claim 1 wherein Z further includes a substituent that includes a reporter ion.

10. A set of crosslinkers of claim 9 wherein said substituent is an isobaric label among the crosslinkers of the set.

11. The crosslinker of claim 9 wherein the substituent is R and R is selected from

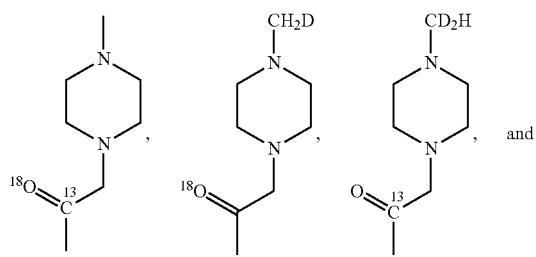

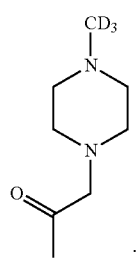

12. The crosslinker of claim 11 which is of the formula:

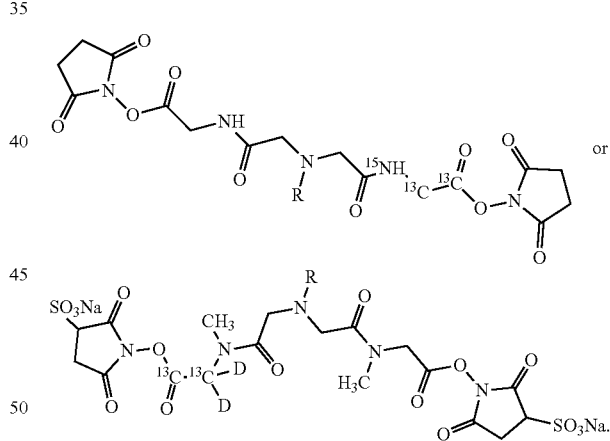

13. A method to identify interacting proteins and the sites of crosslinking in a sample which method comprises
(a) contacting a sample comprising proteins with the crosslinker of claim 1 to obtain crosslinked proteins;
(b) treating said sample with protease to obtain crosslinked peptides;
(c) subjecting said crosslinked peptides to MS under conditions wherein said crosslinked peptides remain substantially intact to obtain MS1;
(d) dissociating said crosslinked peptides under conditions wherein both the bonds represented by Y and peptide bonds within the peptides are cleaved to obtain peptide fragments and portions of said crosslinker coupled to said fragments or peptides;

(e) subjecting said peptide fragments and portions of said crosslinker coupled to said fragments or peptides to MS to obtain MS2;
(f) identifying doublets in said MS2 spectrum as representative of parent peptides of the fragmented portions thereof to ascertain the mass of the parent peptide; and
(g) based on the doublets in (f), analyzing a protein sequence database with a database search algorithm to identify peptides of the appropriate mass that produce theoretical fragmentation patterns that correspond to the acquired MS2 fragmentation pattern.

14. The method of claim 13 wherein said crosslinker further comprises an enrichment handle and wherein subsequent to step (a) and prior to obtaining said MS1, said sample is treated with a binding partner of said enrichment handle to select crosslinked peptides from said sample.

15. The method of claim 13 which further comprises quantitating the relative amounts of at least two pairs of specifically interacting proteins; wherein said method comprises employing a set of at least 2 members which members are crosslinkers of Formula ((1) wherein, in said crosslinkers Z further comprises an label isobaric with respect to said members that include a reporter ion of molecular weight unique to each member of the set;
and wherein said method further comprises in step (f) assessing the relative amounts of the reporter ions generated from each member of the set, thus quantitating the relative amounts of said pairs of interacting proteins.

16. The method of claim 15 which is conducted on at least two samples.

17. The method of claim 16 which is conducted on at least four samples and wherein said set contains at least four members, and wherein each sample is contacted with a crosslinker that is a single member of the set.

18. The method of claim 15 which is conducted on a single sample and wherein one of said pairs of specifically interacting proteins crosslinked with a member of said set is added in known amount.

* * * * *

SEQUENCE LISTING

<160> NUMBER OF SEQ ID NOS: 27

<210> SEQ ID NO 1
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: ACETYLATION
<222> LOCATION: 1

<400> SEQUENCE: 1

Ser Asp Glu Arg Ala Lys Ile Gly Gly Leu Asn Asp Pro Arg Thr Val
1               5                   10                  15
Lys Glu Val Gln Phe Gly Leu Phe Ser Pro Glu Glu Val Arg
            20                  25                  30

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Ala Lys Ile Gly Gly Leu Asn Asp Pro Arg
1               5                   10

<210> SEQ ID NO 3
<211> LENGTH: 16
<212> TYPE: PRT
<213> ORGANISM: Artificial Sequence

```
<220> FEATURE:
<223> OTHER INFORMATION: Synthetic Construct

<400> SEQUENCE: 3

Thr Val Lys Glu Val Gln Phe Gly Leu Phe Ser Pro Glu Glu Val Arg
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Lys Leu Gly Asn Asp His Ser Lys Lys
1               5

<210> SEQ ID NO 5
<211> LENGTH: 23
<212> TYPE: PRT
<213> ORGANISM: Artificial Sequence
<220> FEATURE:
<223> OTHER INFORMATION: Synthetic Construct

<400> SEQUENCE: 5

Lys Val Pro Gln Val Ser Pro Leu Val Glu Val Ser Arg His Lys Pro
1               5                   10                  15

Lys Ala Glu Glu Gln Leu Lys
            20

<210> SEQ ID NO 6
<211> LENGTH: 19
<212> TYPE: PRT
<213> ORGANISM: Artificial Sequence
<220> FEATURE:
<223> OTHER INFORMATION: Synthetic Construct

<400> SEQUENCE: 6

Gly Ala Cys Leu Leu Pro Lys Ile Glu Met Arg Glu Lys Val Leu Ser
1               5                   10                  15

Ser Ala Arg

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

Cys Cys Lys Pro Glu Ser Glu Arg Ser Leu Gly Lys Val Gly Arg
1               5                   10                  15

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Leu Phe Phe His Ala Asp Ile Cys Leu Pro Asp Glu Lys Gln Ile Lys
1               5                   10                  15

Lys Gln Ala Leu Val Glu Leu Leu Lys
```

```
                    20                  25

<210> SEQ ID NO 9
<211> LENGTH: 33
<212> TYPE: PRT
<213> ORGANISM: Artificial Sequence
<220> FEATURE:
<223> OTHER INFORMATION: Synthetic Construct

<400> SEQUENCE: 9

Asn Tyr Gln Glu Ala Lys Asp Ala Phe Leu Gly Ser Phe Leu Tyr Glu
1               5                   10                  15

Tyr Ser Arg Leu Ala Lys Glu Tyr Glu Ala Leu Glu Glu Cys Cys Ala
            20                  25                  30

Lys

<210> SEQ ID NO 10
<211> LENGTH: 28
<212> TYPE: PRT
<213> ORGANISM: Artificial Sequence
<220> FEATURE:
<223> OTHER INFORMATION: Synthetic Construct

<400> SEQUENCE: 10

Asn Tyr Gln Glu Ala Lys Asp Ala Phe Leu Gly Ser Phe Leu Tyr Glu
1               5                   10                  15

Tyr Ser Arg Ala Leu Lys Ala Trp Ser Val Ala Arg
            20                  25

<210> SEQ ID NO 11
<211> LENGTH: 31
<212> TYPE: PRT
<213> ORGANISM: Artificial Sequence
<220> FEATURE:
<223> OTHER INFORMATION: Synthetic Construct

<400> SEQUENCE: 11

Val His Lys Glu Cys Cys His Gly Asp Leu Leu Glu Cys Ala Asp Asp
1               5                   10                  15

Arg Ala Asp Leu Ala Lys Ala Leu Lys Ala Trp Ser Val Ala Arg
            20                  25                  30

<210> SEQ ID NO 12
<211> LENGTH: 23
<212> TYPE: PRT
<213> ORGANISM: Artificial Sequence
<220> FEATURE:
<223> OTHER INFORMATION: Synthetic Construct

<400> SEQUENCE: 12

Leu Ala Lys Glu Tyr Glu Ala Leu Glu Glu Cys Cys Ala Lys Ala Leu
1               5                   10                  15

Lys Ala Trp Ser Val Ala Arg
            20

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Leu Val Asp Leu Lys Val His Lys Ala Leu Lys Ala Trp Ser Val Ala
```

```
-continued 1               5                  10                 15

Arg

<210> SEQ ID NO 14
<211> LENGTH: 21
<212> TYPE: PRT
<213> ORGANISM: Artificial Sequence
<220> FEATURE:
<223> OTHER INFORMATION: Synthetic Construct

<400> SEQUENCE: 14

Ala Glu Phe Val Glu Val Lys Leu Val Asp Leu Lys Ala Leu Lys Ala
1               5                  10                 15

Trp Ser Val Ala Arg
            20

<210> SEQ ID NO 15
<211> LENGTH: 15
<212> TYPE: PRT
<213> ORGANISM: Artificial Sequence
<220> FEATURE:
<223> OTHER INFORMATION: Synthetic Construct

<400> SEQUENCE: 15

Cys Cys Lys Pro Glu Ser Glu Arg Leu Ser Gln Lys Phe Pro Lys
1               5                  10                 15

<210> SEQ ID NO 16
<211> LENGTH: 38
<212> TYPE: PRT
<213> ORGANISM: Artificial Sequence
<220> FEATURE:
<223> OTHER INFORMATION: Synthetic Construct

<400> SEQUENCE: 16

Arg His Pro Tyr Phe Tyr Ala Pro Glu Leu Leu Tyr Tyr Ala Asn Lys
1               5                  10                 15

Tyr Asn Gly Val Phe Gln Glu Cys Cys Gln Ala Glu Asp Lys Glu Lys
            20                  25                 30

Val Leu Ser Ser Ala Arg
        35

<210> SEQ ID NO 17
<211> LENGTH: 24
<212> TYPE: PRT
<213> ORGANISM: Artificial Sequence
<220> FEATURE:
<223> OTHER INFORMATION: Synthetic Construct

<400> SEQUENCE: 17

Leu Ala Lys Glu Tyr Glu Ala Leu Glu Glu Cys Cys Ala Lys Val Lys
1               5                  10                 15

Cys Cys Glu Ser Leu Val Asn Arg
            20

<210> SEQ ID NO 18
<211> LENGTH: 19
<212> TYPE: PRT
<213> ORGANISM: Artificial Sequence
<220> FEATURE:
<223> OTHER INFORMATION: Synthetic Construct

<400> SEQUENCE: 18

Phe Lys Asp Leu Gly Glu Glu His Phe Lys Asp His Lys Ser Glu Ile
```

```
1               5                   10                  15

Ala His Arg

<210> SEQ ID NO 19
<211> LENGTH: 20
<212> TYPE: PRT
<213> ORGANISM: Artificial Sequence
<220> FEATURE:
<223> OTHER INFORMATION: Synthetic Construct

<400> SEQUENCE: 19

Leu Lys Glu Cys Cys Asp Lys Pro Leu Leu Glu Lys Glu Lys Val Leu
1               5                   10                  15

Ser Ser Ala Arg
            20

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Glu Lys Val Leu Ser Ser Ala Arg Leu Ser Gln Lys Phe Pro Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Construct

<400> SEQUENCE: 21

Glu Lys Val Leu Ser Ser Ala Arg Ser Leu Gly Lys Val Gly Arg
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic Construct

<400> SEQUENCE: 22

Cys Cys Lys Pro Glu Ser Glu Arg Glu Lys Val Leu Ser Ser Ala Arg
1               5                   10                  15

<210> SEQ ID NO 23
<211> LENGTH: 19
<212> TYPE: PRT
<213> ORGANISM: Artificial Sequence
<220> FEATURE:
<223> OTHER INFORMATION: Synthetic Construct

<400> SEQUENCE: 23

Cys Ala Ser Ile Gln Lys Phe Gly Glu Arg Ala Leu Lys Ala Trp Ser
1               5                   10                  15

Val Ala Arg

<210> SEQ ID NO 24
<211> LENGTH: 20
<212> TYPE: PRT
<213> ORGANISM: Artificial Sequence
```

```
<220> FEATURE:
<223> OTHER INFORMATION: Synthetic Construct

<400> SEQUENCE: 24

Val Lys Cys Cys Glu Ser Leu Val Asn Arg Cys Ala Ser Ile Gln Lys
1               5                   10                  15

Phe Gly Glu Arg
            20

<210> SEQ ID NO 25
<211> LENGTH: 24
<212> TYPE: PRT
<213> ORGANISM: Artificial Sequence
<220> FEATURE:
<223> OTHER INFORMATION: Synthetic Construct

<400> SEQUENCE: 25

Leu Ala Lys Glu Tyr Glu Ala Leu Glu Glu Cys Cys Ala Lys Cys Ala
1               5                   10                  15

Ser Ile Gln Lys Phe Gly Glu Arg
            20

<210> SEQ ID NO 26
<211> LENGTH: 22
<212> TYPE: PRT
<213> ORGANISM: Artificial Sequence
<220> FEATURE:
<223> OTHER INFORMATION: Synthetic Construct

<400> SEQUENCE: 26

Leu Cys Val Leu His Glu Lys Pro Val Ser Glu Lys Cys Ala Ser Ile
1               5                   10                  15

Gln Lys Phe Gly Glu Arg
            20

<210> SEQ ID NO 27
<211> LENGTH: 26
<212> TYPE: PRT
<213> ORGANISM: Artificial Sequence
<220> FEATURE:
<223> OTHER INFORMATION: Synthetic Construct

<400> SEQUENCE: 27

Ala Glu Glu Gln Leu Lys Val Met Glu Asn Phe Val Ala Phe Val Asp
1               5                   10                  15

Lys Lys Gln Ala Leu Val Glu Leu Leu Lys
            20                  25
```